United States Patent [19]
Liebers et al.

[11] Patent Number: 5,861,941
[45] Date of Patent: Jan. 19, 1999

[54] EYEGLASS DISPLAY RACK WITH VISION TESTER

[75] Inventors: Steven B. Liebers, Norristown, Pa.; Boris B. Liebers, Alfe Menashe, Israel

[73] Assignee: Diversified Products, Inc., Norristown, Pa.

[21] Appl. No.: 818,272

[22] Filed: Mar. 18, 1997

[51] Int. Cl.$^6$ .............................. A61B 3/00; A61B 3/02
[52] U.S. Cl. ...................... 351/245; 351/223; 351/234; 351/243
[58] Field of Search ..................... 351/222, 223, 351/227, 229, 233, 234, 235, 245, 243

[56] References Cited

U.S. PATENT DOCUMENTS

| | | | |
|---|---|---|---|
| 1,228,020 | 5/1917 | Herrick | 351/223 |
| 1,284,103 | 11/1918 | Herrick | 351/223 |
| 1,384,252 | 7/1921 | Giddens | 351/223 |
| 1,416,159 | 5/1922 | Barr | 351/223 |
| 1,437,776 | 12/1922 | Reese et al. | 351/223 |
| 4,896,959 | 1/1990 | O'Brien | 351/203 |
| 5,486,879 | 1/1996 | Barnett | 351/223 |

FOREIGN PATENT DOCUMENTS

| | | | |
|---|---|---|---|
| 2293023 | 3/1996 | United Kingdom | A61B 3/028 |
| WO 95/19133 | 7/1995 | WIPO . | |

Primary Examiner—Huy Mai
Attorney, Agent, or Firm—Caesar, Rivise, Bernstein, Cohen & Pokotilow, Ltd.

[57] ABSTRACT

A vision tester comprising a front wall and a back wall. Printed matter comprising words appears on the back wall, which is approximately 14 inches (35.6 cm.) from the front wall. The printed matter is exposed to ambient light from the top and front. The front wall has an opening through which the user of the vision tester looks. A plurality of magnifying lenses, of different diopter ratings, are selectively positionable behind the opening. Indicia appear to indicate the diopter rating of each lens. The user of the vision tester can determine the diopter rating of the appropriate lens needed for reading by determining which lens renders the printed matter clear and readable.

12 Claims, 8 Drawing Sheets

| DIOPTER |
|---|
| +1.00 |
| +1.25 |
| +1.50 |
| +1.75 |
| +2.00 |
| +2.25 |
| +2.50 |
| +2.75 |
| +3.00 |
| +3.50 |

EYEGLASS DISPLAY RACK WITH VISION TESTER

BACKGROUND OF THE INVENTION

This invention relates to a vision tester, in general, and, more particularly, to a device for use by a consumer in testing his near vision to determine the strength of non-prescription reading glasses the consumer requires.

It is now a common practice to sell non-prescription reading glasses directly to the consumer at pharmacies and other retail outlets. The non-prescription reading glasses are displayed in a retail establishment on free-standing displays.

Typically, a consumer selects a pair of non-prescription reading glasses from the display by trying on a number of pairs until he locates a pair that is suitable, from the standpoint of comfort, magnifying ability and appearance. In order to determine the appropriate magnifying ability for the reading glasses, charts are placed on the displays for the reading glasses. The charts have increasing sizes of print, and the purchaser of the reading glasses is instructed to stand approximately 14 inches (35.6 cm.) from the chart. When viewing the chart, the consumer will look at each line of print, and note the first line of print that appears to be out of focus. By reading across the chart, the consumer can then determine the amount of magnification needed for the reading glasses. The amount is expressed in diopters, an optical unit of measurement.

Once the consumer determines the appropriate amount of magnification needed, the consumer will then view all of the glasses on the display rack that have lenses at the appropriate diopter rating. The consumer can then select a pair of reading glasses which the consumer finds to be attractive and comfortable.

Although the use of the charts can effectively determine the proper amount of magnification needed for the reading glasses, it has been found that the use of the charts is imprecise. Quite often, the consumer will not stand an appropriate distance from the chart and, accordingly, consumers test the reading glasses by simply trying on a large number of reading glasses, of different magnifications, and testing them in connection with reading matter that is hand held by the consumer. The consumer will not always replace the reading glasses that have been tried on in the proper place on the display rack, and eventually, the reading glasses on the display rack are in total disarray.

A hand-held vision tester for non-prescription reading glasses is shown in U.S. Pat. No. 5,486,879. However, that vision tester suffers from a number of disadvantages. It includes a closed tunnel, with a plate at one end of the tunnel having indicia thereon. The plate is light permeable, and the indicia can only be read when the device is positioned in front of a light.

The device of the instant invention exposes the rear wall containing the printed material used for testing vision to the ambient light. There is no tunnel on which the rear wall is mounted.

Another advantage of the instant invention, as compared to that shown in U.S. Pat. No. 5,486,879, is that the degree of magnification for each lens is the same for both the right eye and left eye. In U.S. Pat. No. 5,486,879, the lenses are adjustable independently of each other. If one lens should indicate a certain power of magnification for the left eye and the lens for the right eye indicates a different power of magnification, the device is inappropriate for non-prescription reading glasses. All non-prescription reading glasses contain lenses of the same degree of magnification. In the instant invention, the lenses are arranged to be certain that the same degree of magnification will be used for both eyes. It is not possible to have different degrees of magnification for each eye.

Another advantage of the instant invention is that it is formed as part of a display rack for non-prescription reading glasses. This permits the consumer to test her vision at the same location as the location of the non-prescription reading glasses. Since the vision tester is formed as part of the display rack, there is little likelihood of damage caused by dropping or mishandling, as could occur with the hand-held vision tester of U.S. Pat. No. 5,486,879.

The device of this invention will precisely measure the magnification power necessary for the reading glasses of each consumer. By utilizing the device, the consumer can accurately determine the appropriate diopter rating for the reading glasses, and try on only those reading glasses having that diopter rating. Since the reading glasses will be removed from only one segment of the display, there is a much greater probability that the reading glasses will be returned to that segment after they are tried on, if they are not purchased.

SUMMARY OF THE INVENTION

A vision tester comprising a front wall and a back wall. On the back wall, which is approximately 14 inches (35.6 cm.) from the front wall, printed matter comprising words appears. The printed matter is exposed to ambient light from the top and front. The front wall has an opening through which the user of the vision tester looks. A plurality of magnifying lenses, of different diopter ratings, are selectively positionable behind the opening. Indicia appear to indicate the diopter rating of each lens. The user of the vision tester can determine the diopter rating of the appropriate lens needed for reading by determining which lens renders the printed material clear and readable.

DESCRIPTION OF THE DRAWINGS

Objects and many of the attendant advantages of this invention will become readily appreciated as the same becomes better understood by reference to the following detailed description, when considered in connection with the accompanying drawing, wherein.

DETAILED DESCRIPTION OF THE PREFERRED EMBODIMENT

Figure 1:
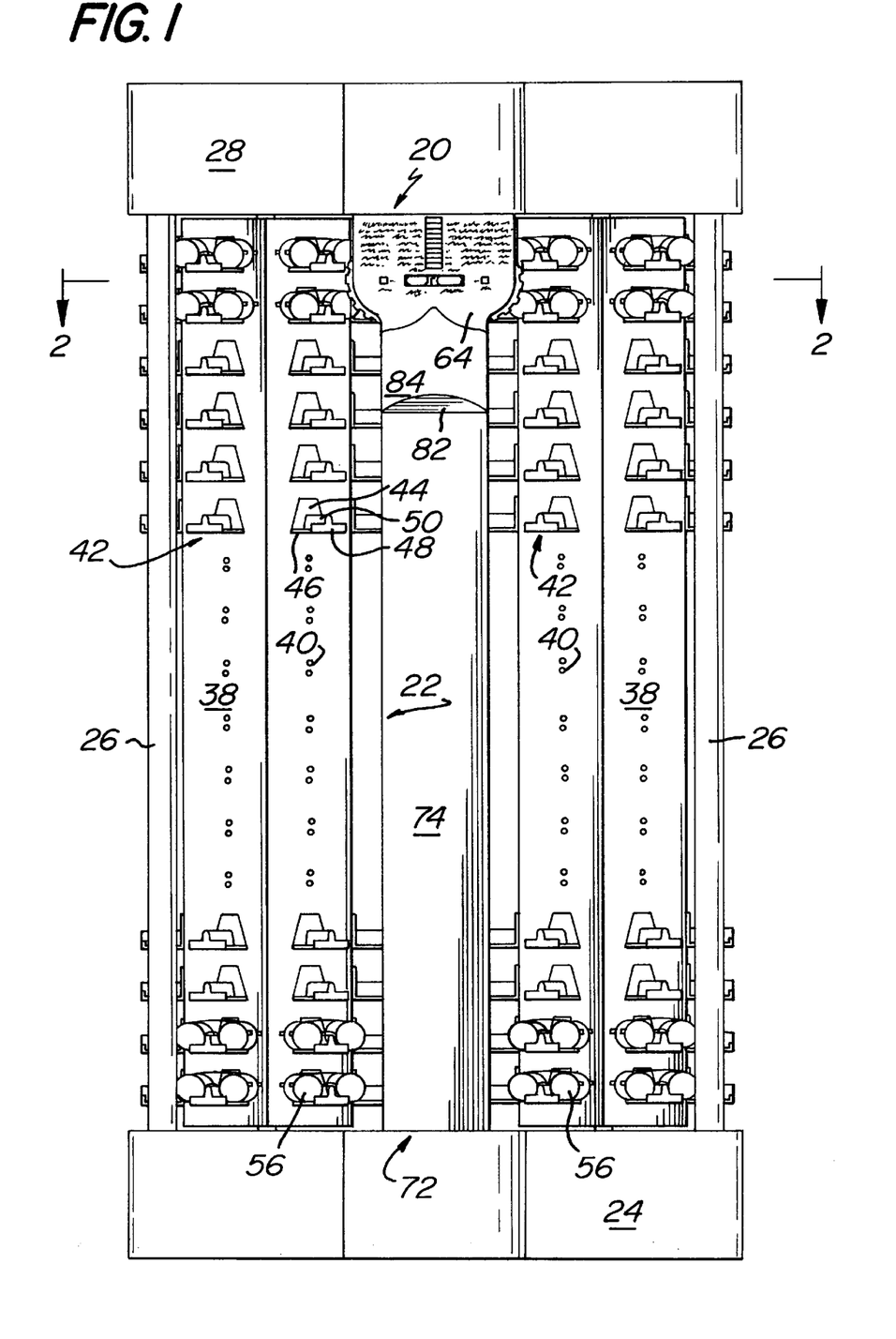
FIG. 1 a front elevational view of an eyeglass display rack which incorporates the vision tester of this invention.

Referring now in greater detail to the various figures of the drawing, wherein like reference characters refer to like parts, a vision tester embodying the present invention is generally shown at 20 in FIG. 1. The vision tester 20 is mounted on a non-prescription reading glass display rack 22.

Figure 2:
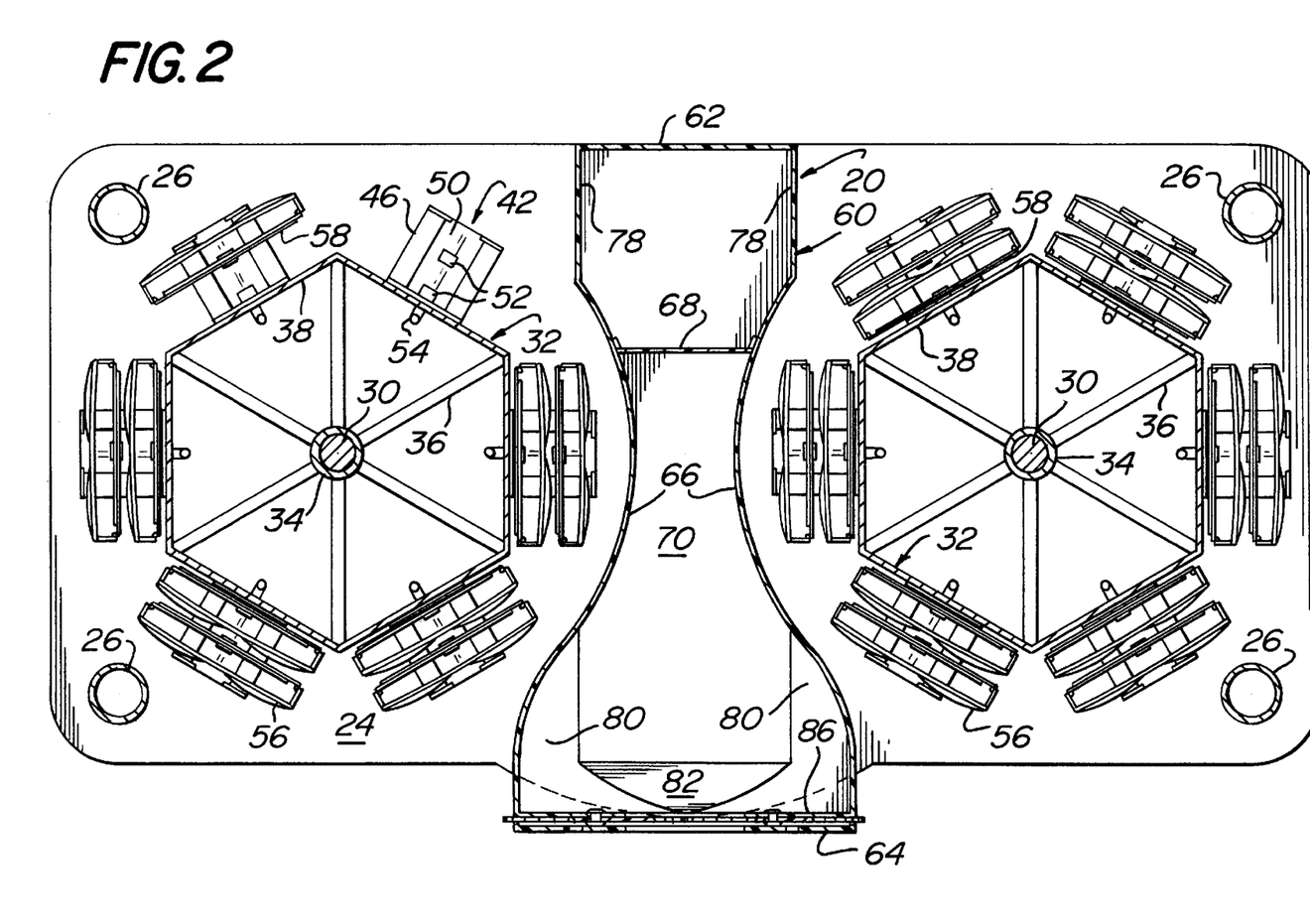
FIG. 2 is an enlarged sectional view taken along the line 2—2 of FIG. 1.

Referring to FIGS. 1 and 2, the display rack 22 includes a base 24 and four vertical support poles 26. A top 28 is supported by poles 26 (FIG. 1). A pair of rods 30 (FIG. 2) extend vertically upward from base 24 to top 28, and are secured in the top and base.

An eyeglass display member 32 is rotatably mounted on each rod 30. Each eyeglass display member includes a center shaft 34, which is rotatably mounted on rod 30, and supports 36, which are secured to shaft 34 and extend radially therefrom. Walls 38 are secured to and supported by supports 36, and extend from the base 24 to the top 28. Each wall 38 has a plurality of pairs of openings 40, which are vertically spaced on the wall. Secured in each pair of openings 40 is an eyeglass support 42. The eyeglass support 42 is molded from plastic, and includes a rear wall 44, a base 46 and a front wall 48. A hollow rib 50 projects upwardly from and is unitary with base 46. As seen in FIG. 2, rib 50 has a pair of spaced slots 52 formed in the top surface thereof. Support 42 is secured on a wall 38 by inserting an upwardly open hook 54 (FIG. 2) in an upper opening 40 in wall 38 and inserting a pin (not shown) in the lower opening 40. Further details on the structure of support 42 can be found in U.S. Pat. Design No. 374,786.

Non-prescription reading glasses that are to be sold are mounted on supports 42. The glasses have the temples folded so that they are parallel to the frame. The glasses, which are shown at 56 in FIGS. 1 and 2, are then placed over the supports so that the ribs 50 are received in the bridges of the frames. The temples, shown at 58 in FIG. 2, are then received in the slots 52. The resting of the bridges on the ribs and the engagement of the temples in the slots holds the eyeglasses 56 in place when the eyeglass display members are rotated.

Tags (not shown) are placed on each pair of reading glasses 56, to identify the power of the reading glasses, by diopters, and, if desired, by the power of magnification. As is customary in the art, the tags are also color coded, in accordance with the diopters, to have the glasses of the desired diopter rating readily identifiable. The color coding can also be used to segregate all glasses of a certain diopter rating in a given area of the display rack.

The display rack shown in FIGS. 1 and 2 is merely exemplary of the many display racks available for displaying and vending non-prescription reading glasses. The actual structure of the display rack does not form a part of this invention. Other racks and supports for the non-prescription reading glasses can be used in carrying out this invention, such as those disclosed in U.S. Pat. Nos. 4,976,532 and 5,100,006.

The novelty of this invention resides in the vision tester 20. The vision tester can be secured as an integral part of the display rack shown in the drawings, or as an integral part of any other display rack known to the art. It can also be placed on a support separate from a display rack. In all of the embodiments of the invention disclosed, the vision tester 20 includes a housing 60 (FIG. 2) having a rear wall 62, a front wall 64 and side walls 66. As seen in FIG. 2, the side walls 66 are concave, in order to permit the rotation of the display members 32 around rods 30.

A back wall 68 is mounted between side walls 66, and inwardly of rear wall 62. Back wall 68, which has words 69 printed thereon, is parallel to rear wall 62 and front wall 64.

Figure 3:
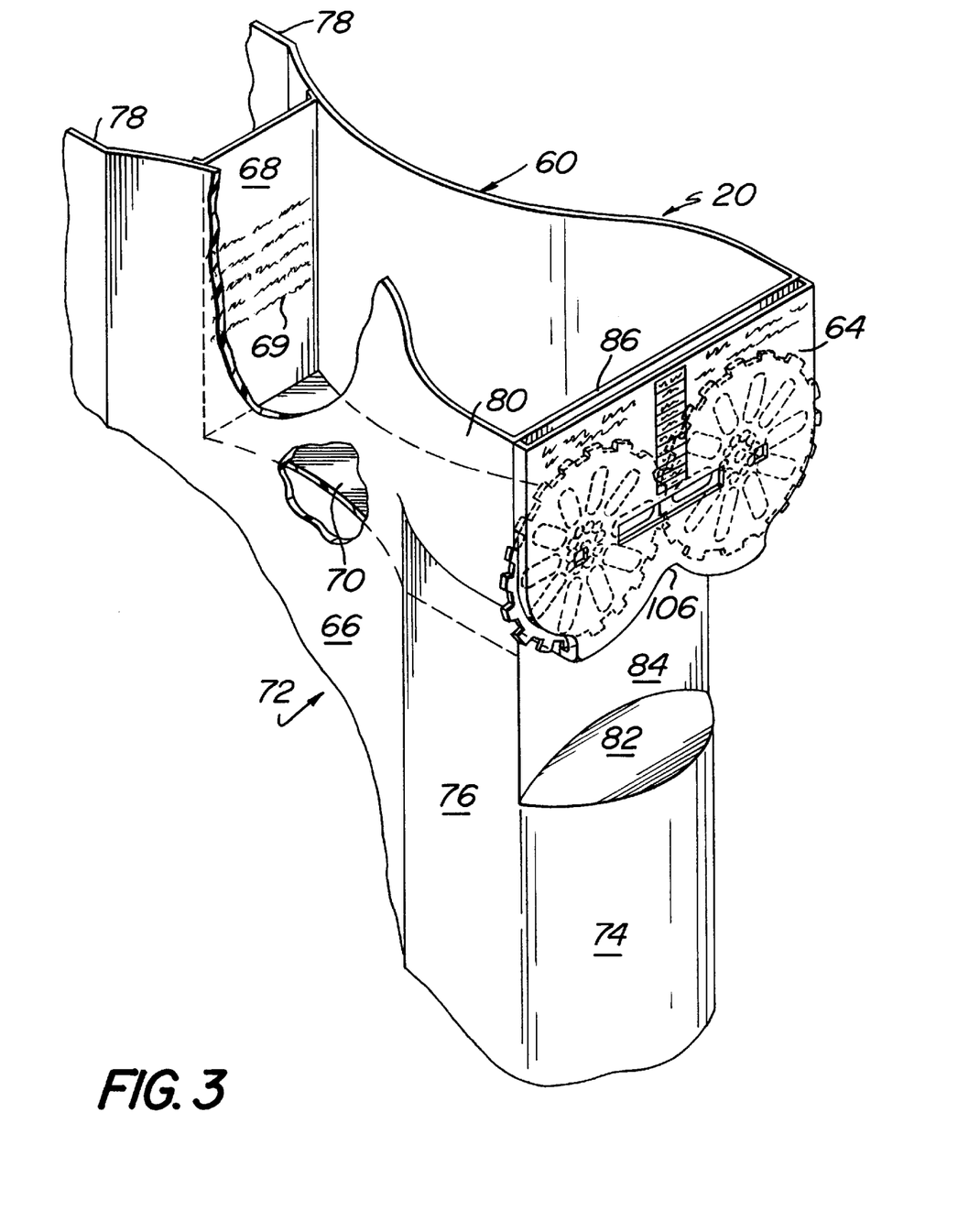
FIG. 3 is a perspective view, partially broken away, of a first embodiment of the vision tester of this invention.

Housing 60 includes a floor 70 (FIGS. 2 and 3). The housing 60 is positioned at the top of, and is unitary with, support 72. Support 72 extends from the top of base 24 to top 28 (FIG. 1). As seen in FIG. 3, the top of housing 60 is open, and there is a central opening in top 28. Light in the room above the display fixture 22 can illuminate the interior of housing 60 and the words 69.

Support 72 has an arcuate front wall 74 and parallel side walls 76 (one shown in FIG. 3) projecting rearwardly therefrom. Side walls 76 are unitary with side walls 66. Rear wall 62 has side walls 78 (FIGS. 2 and 3) projecting inwardly therefrom. Walls 62, 78, 66, 76 and 74 extend downwardly to base 24, and all of these walls, with the exception of walls 74 and 76, have an upper terminus in housing 60.

The tops of side walls 76 flare outwardly, as shown at 80 in FIGS. 2 and 3. Arcuate wall 74 terminates in an inclined ledge 82. Wall 84 projects upwardly from ledge 82. A wall 86 is unitary with and extends across flared walls 80.

Figure 6:
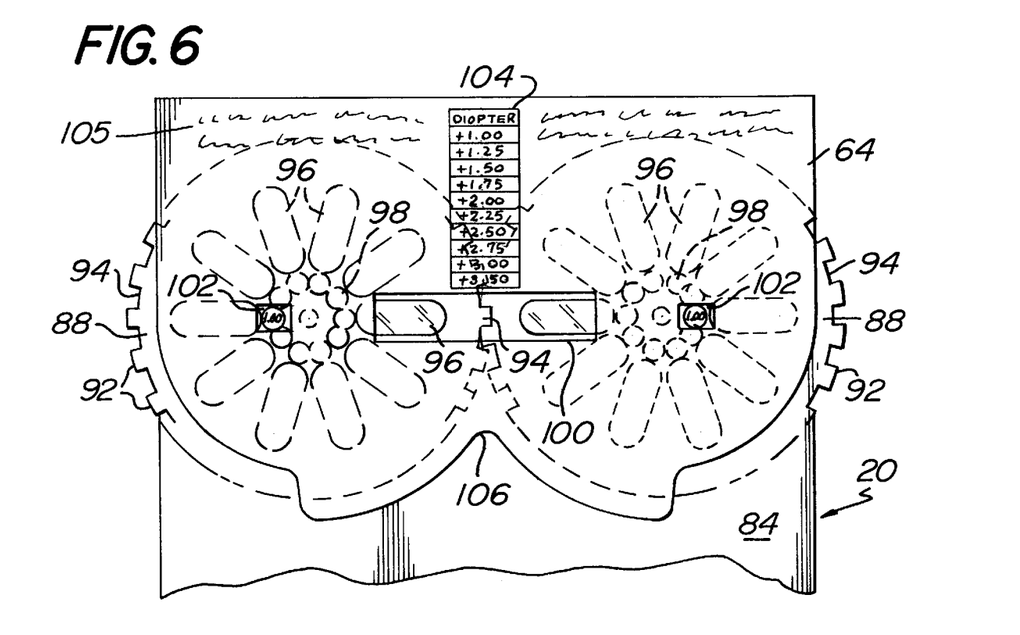
FIG. 6 is a front elevational view of the vision tester of FIG. 3.
Figure 9:
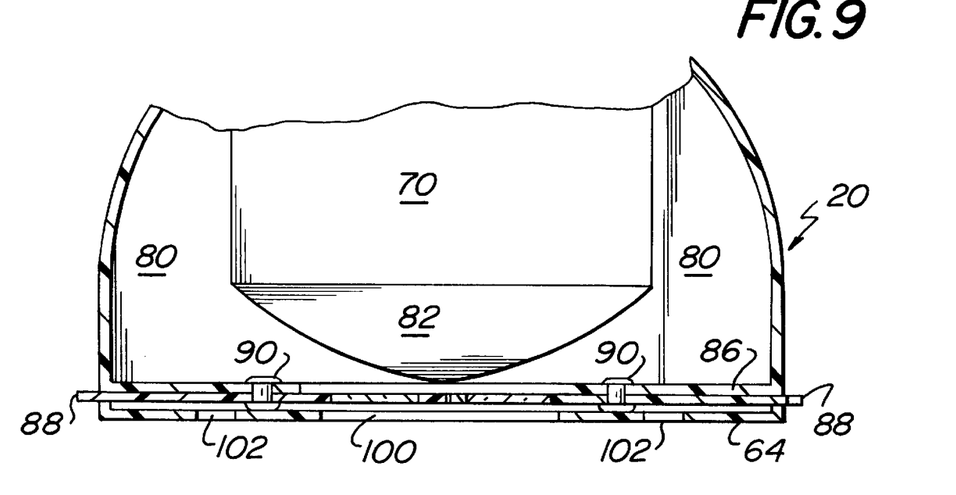
FIG. 9 is an enlarged top sectional view of the front of the vision tester shown in FIG. 2; and, FIG. 10 is an enlarged front elevational view of the color-coordinating chart used with each of the embodiments of the vision tester.

Further details on the vision tester 20 are best seen in FIGS. 6 and 9. Discs 88 are rotatably mounted relative to wall 86 and front wall 64 by rivets 90 that pass through openings in wall 86 and discs 88 (FIG. 9). The outer edge of each disc 88 includes a plurality of equally-spaced teeth 92, separated by equally-spaced openings 94 (FIG. 6). As seen in FIG. 6, as the discs 88 are rotated, a tooth 92 of one disc is received in an opening 94 of the other disc. Thus, the teeth and openings mesh as gears. Accordingly, when one disc 88 is rotated, the other disc will be simultaneously rotated at the same speed and the same amount, by the meshing of the teeth and openings.

Each disc 88 includes a plurality of equally-spaced, radial openings in which are secured lenses 96. Each lens 96 is of a different magnification and, accordingly, has a different diopter rating. Inwardly of each lens 96 is a segment 98 having printed thereon the diopter rating of the associated lens.

Front wall 64 has a central rectangular opening. Wall 64 further includes openings 102 on opposite sides of opening 100, and in alignment with opening 100. A pair of aligned lenses 96 are visible through opening 100, and the diopter rating for the lenses, which is identical for both lenses, is visible through openings 102. A diopter chart 104 is secured on the front face of wall 64. Instructions for using the vision tester are placed on wall 64, as shown at 105.

Figure 10:
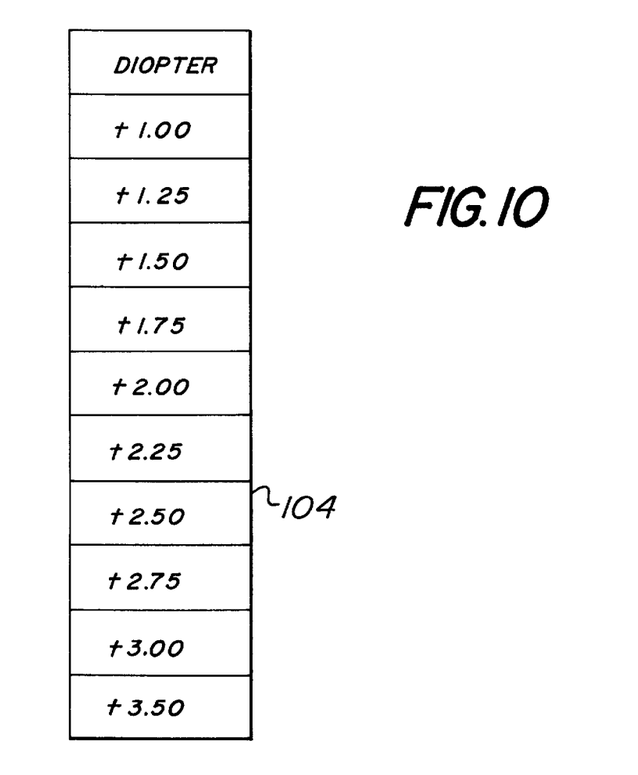

An enlarged showing of the diopter chart 104 appears in FIG. 10. As seen therein, ten rectangles appear on the chart, with each of the rectangles having a different diopter rating. The diopter ratings correspond to the ratings of the lenses 96. The color of the rectangle for each diopter rating is different from all of the other colors for the rectangles for the diopter ratings. The non-prescription reading glasses on the display rack are segregated by diopter rating, and the segment of the display rack having a particular diopter rating is color-coded to match the color for that rating appearing on chart 104. This facilitates the refilling of inventory by the store owner and the selection of eyeglasses by the consumer.

The vision tester 20 is used by the consumer's standing in front of display rack 22 and placing his eyes adjacent opening 100. An opening identical in size, shape and placement to opening 100 is formed in wall 86. A notch 106 is formed in the bottom of wall 64. When the consumer places his eyes at slot 100, his nose will be in notch 106. The lower portion of the consumer's head will be in the recess formed between walls 74 and 84.

When the consumer is looking through opening 100 toward back wall 68, the printed words 69 on back wall 68 can be viewed through a pair of aligned lenses 96. The consumer then rotates one of the discs 88 to change the lens appearing at opening 100. Through the use of the gear teeth 92, the rotation of one disc 88 will automatically rotate the other disc 88, in view of the meshing of the gear teeth, as shown in FIG. 6. The consumer continues changing the lenses at opening 100 until the print on back wall 68 is clear and is in focus. The magnification of the lenses at this point is the appropriate magnification for the consumer's reading glasses. In this connection, the rear wall is approximately 14 inches (35.6 cm.) from the lenses, which is the normal distance optical professionals use to determine a prescription for reading glasses. The distance can be varied to any distance that is effective for determining the appropriate magnification, as is known to those skilled in the art. The vision tester of this invention may be used at distances ranging from approximately eight inches (20.3 cm.) to the back wall 68 to approximately 20 inches to the back wall 68 (50.8 cm.).

Once the appropriate lens 96 is determined, the consumer then views the openings 102 (FIG. 6) to determine the appropriate diopter rating for the selected lenses. By way of example, the diopter rating shown in FIG. 6 is +1.00. The consumer then views the chart 104 (FIGS. 6 and 10). In doing so, the consumer will note the color which signifies all of the reading glasses having a diopter rating of +1.00. These eyeglasses are in a segregated area of the display rack 22, and each pair of eyeglasses contains an identifying tag which shows the degree of magnification and the diopters. The tag will also bear the same color as that indicated on chart 104 for glasses having the specific diopter rating. Color-coding systems have been used in the past in connection with the vending of non-prescription reading glasses. However, they were used with the prior art methods of determining the appropriate diopter rating for the reading glasses.

Figure 4:
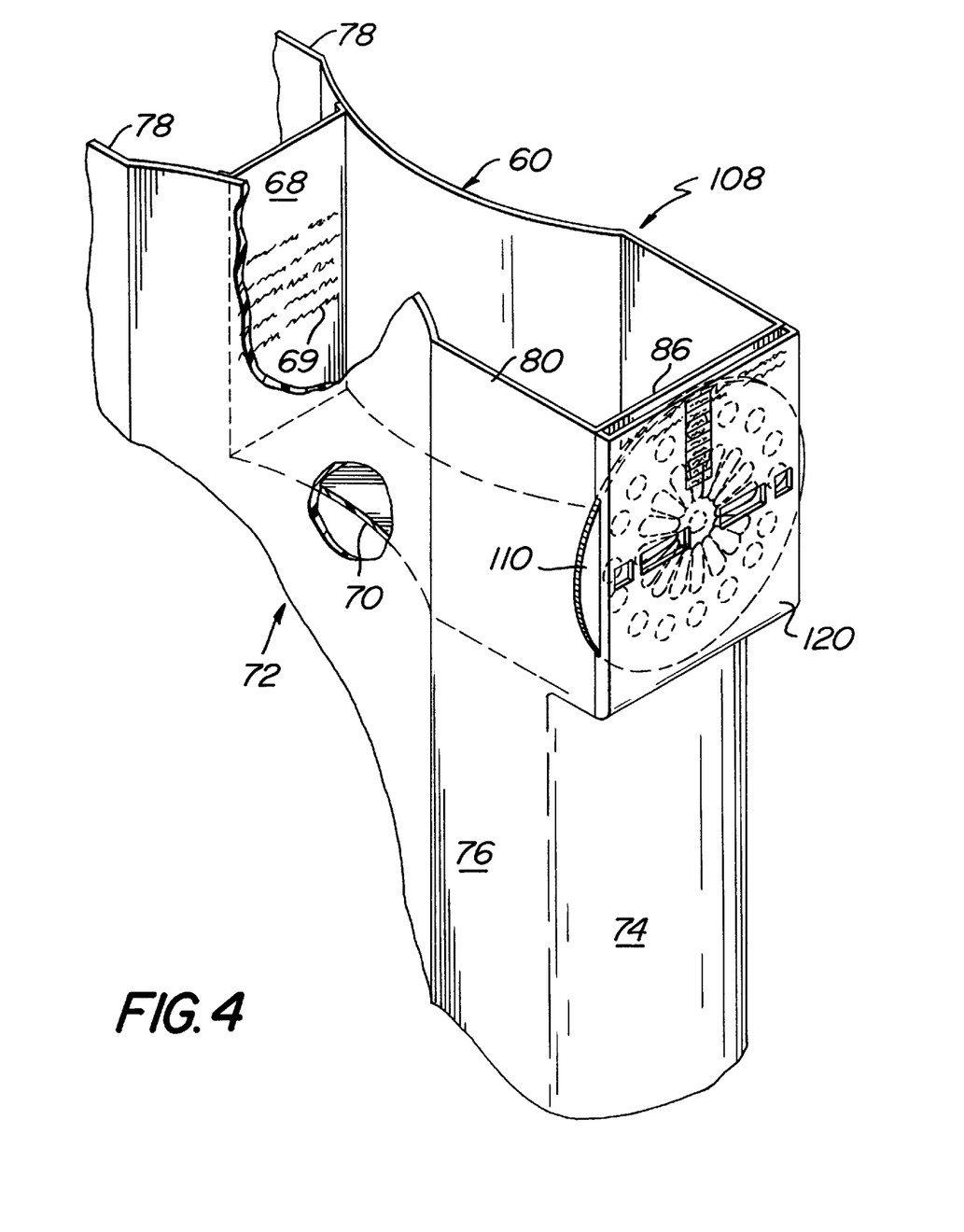
FIG. 4 is a perspective view, partially broken away, of a second embodiment of the vision tester of this invention.
Figure 7:
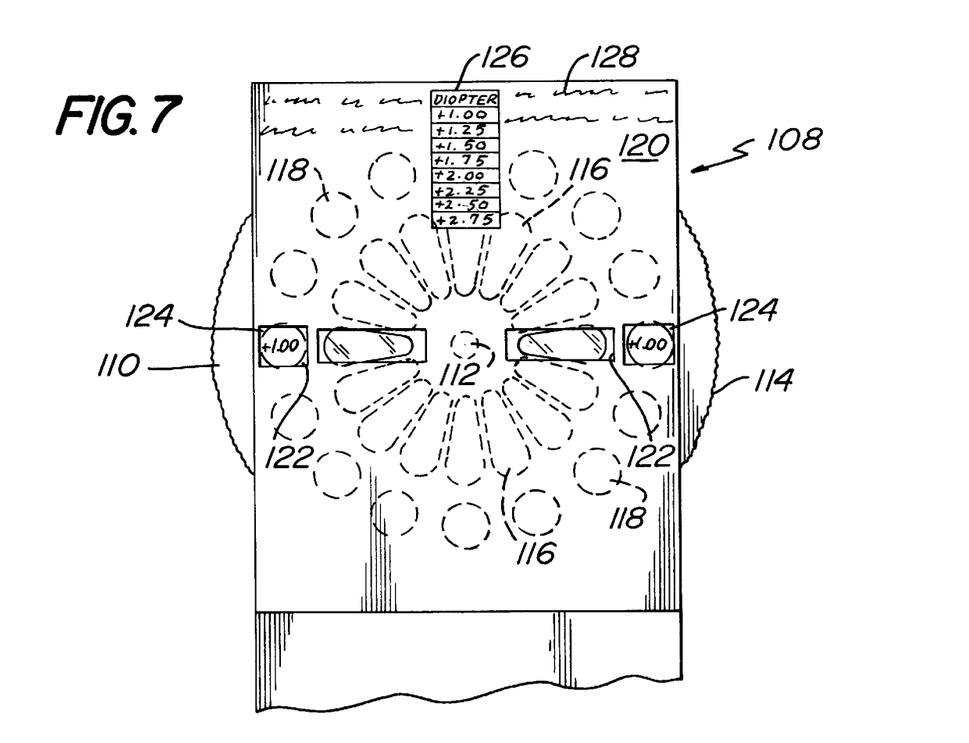
FIG. 7 is a front elevational view of the vision tester of FIG. 4.

A second embodiment of the vision tester of this invention is generally shown at 108 in FIG. 4. The reading tester 108 is mounted on a support 72 that is substantially identical to that used with reading tester 20. Additionally, the housing 60 is substantially identical to the housing used with reading tester 60. The difference in the two reading testers resides in the use of a single disc 110, instead of the pair of mating discs 88. Disc 110 is rotatably mounted on wall 86 by rivet 112 (FIG. 7). Disc 110 has a notched circumference 114, to facilitate the rotation of the disc. A plurality of openings are formed in disc 110, and a lens 116 is secured in each opening. The lenses 116 extend radially from rivet 112. Each diametrically-opposed pair of lenses has the same magnification power and, accordingly, the same diopter rating. A printed segment 118 is radially aligned with each lens 116. The printed segment contains the diopter rating of the associated lens.

A front wall 120 is positioned over disc 110. Front wall 120 includes a pair of aligned openings 122. An opening 124 is formed in wall 120 adjacent each opening 122. A diopter chart 126 is secured on wall 120. Instructions 128 are printed on wall 120, to instruct the consumer in the use of the vision tester 108.

In use, a consumer will align her eyes with openings 122. Openings identical in size, shape and placement to openings 122 are formed in wall 86. The consumer will then rotate disc 110 until lenses having the appropriate magnification appear. The appropriate magnification is determined by viewing the printed material on back wall 68, until it is clear and legible. Since diametrically-opposed lenses on disc 110 have the same diopter rating, the lenses' position behind openings 122 will both have the same diopter rating. When the appropriate lenses are in place, the diopter rating for the lenses can be determined from the printed segments appearing in openings 124. Thereafter, the consumer can consult the chart 126 to determine the color coding for the appropriate reading glasses.

In the embodiment of the invention shown in FIGS. 4 and 7, there is no provision for a nose notch 106. The structure of the disc does not provide space for this. Additionally, it is unnecessary to have the flared housing walls 80 of embodiment 20. Front wall 74 of the support has the same dimensions up to the housing 60, and it is unnecessary to provide the recess formed by wall 84 and ledge 82.

Because of size constrictions, only eight sets of lenses are used on disc 110. To have more than eight sets of lenses would require a disc diameter that would be too large to use conveniently. Accordingly, in the embodiment of FIGS. 4 and 7, only eight diopter ratings appear on the chart 126, whereas ten diopter ratings can be used with vision tester 20, and all ten ratings appear on the chart 104.

Figure 5:
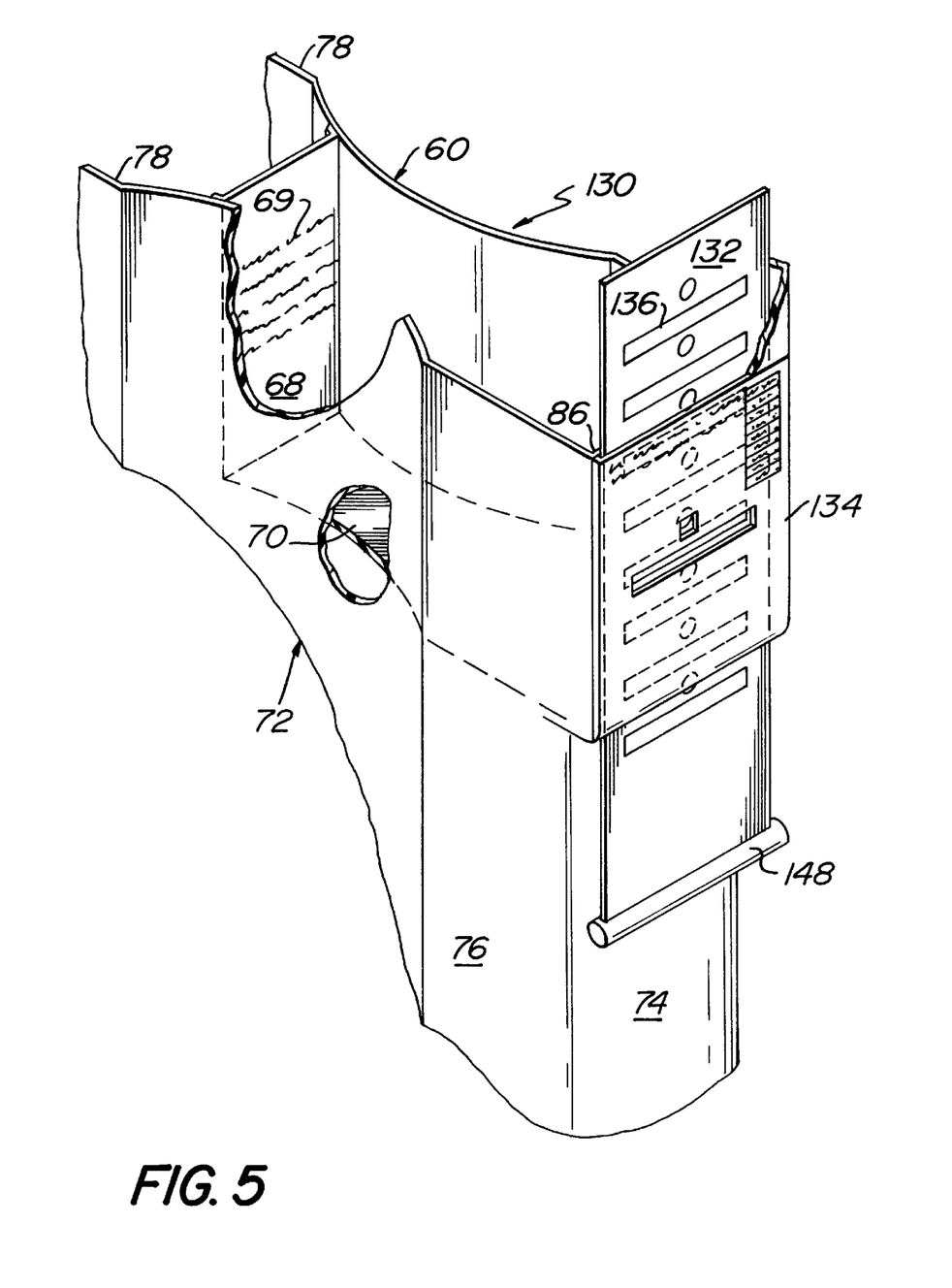
FIG. 5 is a perspective view, partially broken away, of a third embodiment of the vision tester of this invention.
Figure 8:
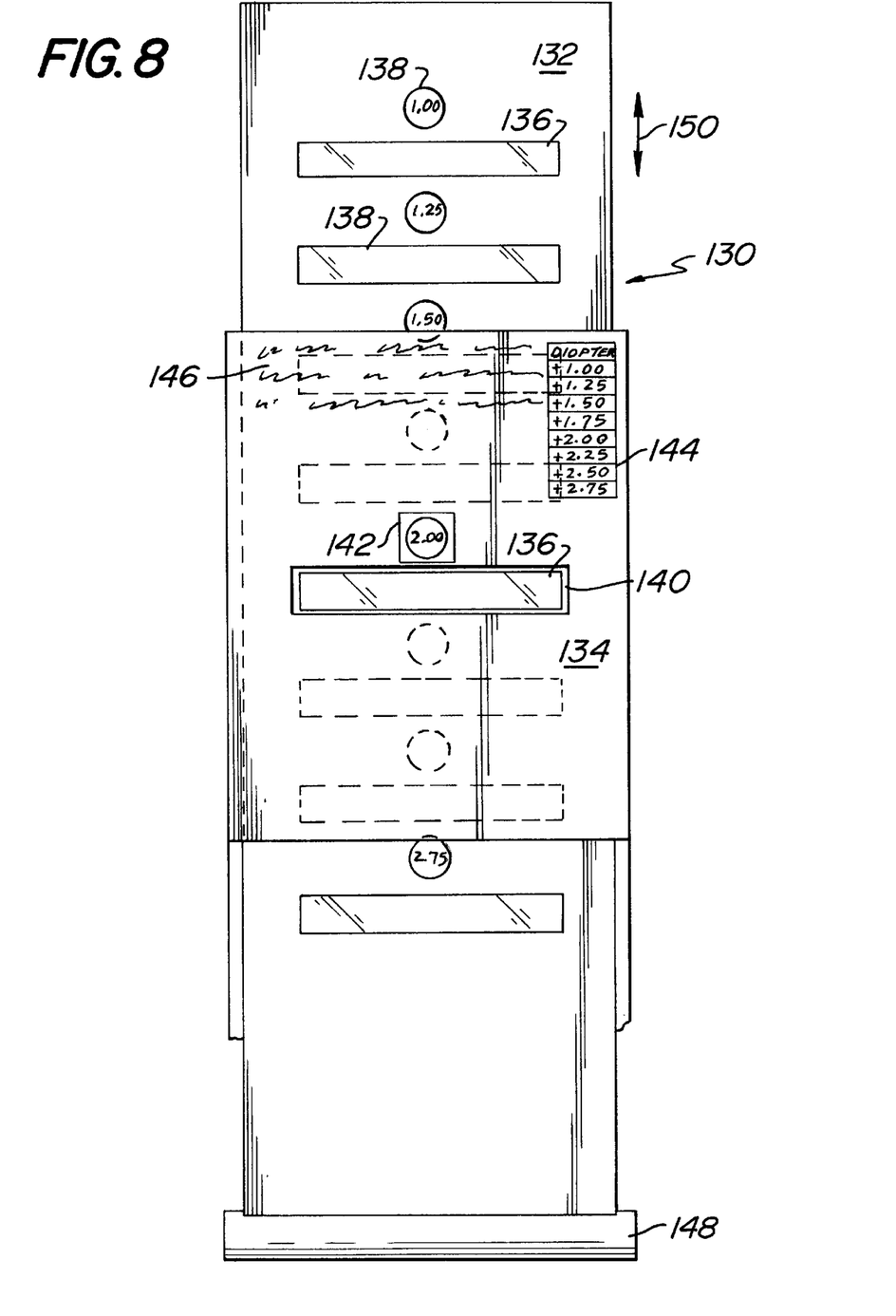
FIG. 8 is a front elevational view of the vision tester of FIG. 5.

A third embodiment of the vision tester of this invention is generally shown at 130 in FIGS. 5 and 8. Embodiment 130 is similar to the other embodiments, in that it includes housing 60 and is mounted on support 72. In embodiment 130, there are no discs for the lenses. Instead, the lenses are mounted in a rectangular, rigid sheet 132. Rigid sheet 132 is slidably and frictionally secured between wall 86 and front wall 134.

Rigid sheet 132 contains a plurality of vertically-spaced openings, with a lens 136 secured in each opening. Each lens 136 differs from the other lenses in its magnification power and, accordingly, its diopter rating. A printed segment 138 is positioned above each lens 136. The printed segment 136 contains the diopter rating for the associated lens.

Front wall 134 has a rectangular opening 140 similar in shape and slightly larger in size than each lens 136. Wall 134 contains a smaller opening 142 positioned above opening 140. A diopter chart 144 is secured on front wall 134. Printed instructions 146 for the use of the vision tester appear on wall 134.

Vision tester 130 is used by a consumer by his placing his eyes in front of opening 140. An opening identical in position, size and shape to opening 140 is formed in wall 86. The consumer then grasps rod 148 that is secured to the bottom of rigid sheet 132, and raises or lowers the sheet, as indicated by arrow 150 in FIG. 8. The raising and lowering of the sheet places different lenses 136 behind opening 140.

The consumer changes the lenses 136 until the print on wall 68 is clear and legible. The consumer then notes the diopter rating for the appropriate lens, by looking through opening 142. Reference to the diopter chart 144 will then provide the consumer with the appropriate color to locate the available reading glasses having that diopter rating.

In embodiment 130, as in embodiment 108, only eight different lenses are used. Here again, the limitation on the number of lenses is based on the convenient height for the rigid sheet 132. Having more lenses could make it difficult for a consumer to readily move the sheet up and down, in order to determine the correct lenses. However, it is possible to have a larger sheet or have slightly smaller lenses, to thereby increase the number of available lenses that could be tested.

It is thus seen that the vision tester of this invention provides a convenient and easy-to-use device for permitting a consumer to determine the appropriate magnification for his non-prescription reading glasses. The vision tester can be made an integral part of a display rack for the reading glasses, or it can be placed on a separate support to be used in connection with a display rack for the reading glasses. The support 72 for the vision tester can be made of any material that can be formed into the desired shape. Preferably, the support and the associated housing 60 are molded from plastic. Molded paperboard can also be used. These materials are generally opaque.

The openings in the front wall of the vision tester can be set at any desired height, or the vision tester can be placed on a support that will provide an adjustable height for the openings. When the openings are at a pre-set height, a height of approximately five feet (1.52 m.) should be the most effective height. Taller people can easily bend their knees to use that height, and that height should be sufficiently low for virtually all people who will be using the vision tester.

Without further elaboration, the foregoing will so fully illustrate this invention that others may, by applying current or future knowledge, readily adapt the same for use under various conditions of service.

We claim:

1. In combination with a display rack holding plural pairs of non-prescription reading glasses so that they may be seen by a customer, a vision tester for determining the strength of the reading glasses required by the customer, said vision tester comprising a housing having an opening through which ambient light may pass, a front wall, and a back wall, said back wall having printed matter appearing thereon and which is arranged to be illuminated by ambient light through said opening of said housing, said front wall having a pair of eye openings through which the customer can look, a plurality of pairs of magnifying lens portions, and respective indicia indicating the magnify power of each of said pairs of magnifying lens portions, all of said pairs of magnifying lens portions being of different diopter ratings, each portion of each pair of said magnifying lens portions being of the same diopter rating as the other portion of said pair, said pairs of magnifying lens portions being mounted on movable means having peripheral portions extending beyond said housing arranged to be readily grasped directly by either hand of the user to selectively move said movable means to bring any particular pair of magnifying lens portions into alignment with said eye openings, whereupon the customer can look through said eye openings and the aligned lens portions to view said printed matter appearing on said back wall, said indicia indicating the magnifying power of each pair of magnifying lens portions being coupled to said movable means, whereupon indicia indicating the diopter rating of the particular pair of magnifying lens portions which is aligned with said eye openings is readily visible to the customer.

2. The combination of claim 1, wherein said vision tester is positioned on a support adjacent said display rack.

3. The vision tester of claim 2, wherein said display rack and said support are mounted on a common base.

4. The combination of claim 2, wherein the support for said vision tester is positioned between two display racks.

5. The combination of claim 1, wherein said pairs of magnifying lens portions comprise pairs of lenses arranged on a disc, said disc forming said movable means and being rotatably mounted relative to said front wall, with each pair of lenses having the same magnifying power, and the lenses of each pair being diametrically opposed on said disc.

6. The combination of claim 5, wherein a pair of openings are formed in said front wall, with each pair of lenses being selectively positionable behind said pair of eye openings.

7. The combination of claim 1, wherein said pairs of magnifying lens portions are mounted in a rigid sheet, with each pair of said pairs of magnifying lenses being vertically spaced from an adjacent pair on said rigid sheet and said rigid sheet being vertically movable relative to said front wall in order to bring different pairs of magnifying lens portions into alignment with said eye openings.

8. The combination of claim 1 wherein said movable means comprises a pair of discs rotatably mounted on said front wall.

9. The combination of claim 8, wherein means are provided for causing the rotation of one disc when the other disc is rotated.

10. The combination of claim 9, wherein said means for causing the simultaneous rotation of said discs comprise gear teeth formed in the circumference of each disc, said gear teeth meshing when the discs are rotated.

11. The combination of claim 1, wherein said rear wall is approximately 14 inches (35.6 cm.) from said lens portions.

12. The combination of claim 1, wherein said eye opening is approximately five feet (1.52 m.) from the floor.

* * * * *